United States Patent [19]

Hwang-Felgner et al.

[11] Patent Number: 5,151,265
[45] Date of Patent: Sep. 29, 1992

[54] GAMMA INTERFERON FORMULATION

[75] Inventors: Jiin-Yu Hwang-Felgner, Los Altos; Richard E. Jones, Palo Alto, both of Calif.; James F. Maher, Broken Arrow, Okla.

[73] Assignee: Genentech, Inc., South San Francisco, Calif.

[21] Appl. No.: 514,392

[22] Filed: Apr. 25, 1990

Related U.S. Application Data

[63] Continuation of Ser. No. 116,434, Nov. 3, 1987, abandoned.

[51] Int. Cl.$^5$ .............. A61K 37/66; C07K 13/00
[52] U.S. Cl. .................. 424/85.5; 530/351; 435/69.51
[58] Field of Search .......... 424/85.5; 530/351

[56] References Cited

U.S. PATENT DOCUMENTS

| | | | |
|---|---|---|---|
| 4,100,150 | 7/1978 | Cartwright et al. | 424/85.4 |
| 4,469,228 | 9/1984 | Zupon et al. | 206/568 |
| 4,483,849 | 11/1984 | Carter et al. | 424/85.4 |
| 4,496,537 | 1/1985 | Kwan et al. | 424/85.7 |
| 4,647,454 | 3/1987 | Cymbalista et al. | 424/85.6 |
| 4,659,570 | 4/1987 | Terano et al. | 424/85.5 |
| 4,675,184 | 6/1987 | Hasegawa et al. | 424/85.5 |
| 4,714,611 | 12/1987 | Tetsuo et al. | 424/85.5 |
| 4,751,078 | 6/1988 | Nagabhushan et al. | 424/85.5 |
| 4,824,674 | 4/1989 | Becker et al. | 424/85.7 |
| 4,847,079 | 7/1989 | Kwan et al. | 424/85.7 |
| 4,911,908 | 3/1990 | Estis et al. | 424/85.7 |

FOREIGN PATENT DOCUMENTS

| | | |
|---|---|---|
| 0080879 | 6/1983 | European Pat. Off. . |
| 0089245 | 9/1983 | European Pat. Off. . |
| 0123291 | 10/1984 | European Pat. Off. . |
| 0133767 | 3/1985 | European Pat. Off. . |
| 146354 | 6/1985 | European Pat. Off. . |
| 0150067 | 7/1985 | European Pat. Off. . |
| 0177910 | 4/1986 | European Pat. Off. . |
| 0196203 | 10/1986 | European Pat. Off. . |
| 196203 | 10/1986 | European Pat. Off. . |
| 0215658 | 3/1987 | European Pat. Off. . |
| 0219073 | 4/1987 | European Pat. Off. . |
| 0258683 | 3/1988 | European Pat. Off. . |
| 0270799 | 6/1988 | European Pat. Off. . |
| 0284249 | 9/1988 | European Pat. Off. . |
| 0162332 | 11/1989 | European Pat. Off. . |
| 3520228 | 12/1985 | Fed. Rep. of Germany . |
| 58-092691 | 6/1983 | Japan . |
| 59-181224 | 10/1984 | Japan . |
| 60087300 | 5/1985 | Japan . |
| 60-260523 | 12/1985 | Japan . |
| 61-137828 | 6/1986 | Japan . |
| 62-030708 | 2/1987 | Japan . |
| 8809674 | 12/1988 | World Int. Prop. O. . |
| 8902750 | 4/1989 | World Int. Prop. O. . |

OTHER PUBLICATIONS

Wang et al., (1988) Journal of Parental Science & Technology, vol. 42, 54–526.
Blalock et al., *Cellular Immunology* 49, 390–394 (1980).
Patent Abstracts of Japan, vol. 9, No. 28 (C–264)[1751] Feb. 6, 1985.
Patent Abstracts of Japan, vol. 11, No. 139 (C–420)[2586] May 7, 1987.
Sedmak et al., *Biol. Med.* 41, 274–279 (1981) (Abstract Only).

*Primary Examiner*—Robert A. Wax
*Assistant Examiner*—R. Keith Baker
*Attorney, Agent, or Firm*—Ginger R. Dreger

[57] ABSTRACT

A liquid pharmaceutical composition comprising an effective amount of non-lyophilized gamma-interferon. The liquid pharmaceutical composition which additionally includes a buffer capable of maintaining the pH of the liquid composition within the range of 4.0 to 6.0, a stabilizing agent and a non-ionic detergent.

17 Claims, No Drawings

GAMMA INTERFERON FORMULATION

This is a continuation of co-pending application Ser. No. 07/116,434 filed on Nov. 3, 1987 now abandoned.

FIELD OF THE INVENTION

This invention relates to a stable biologically active gamma-interferon liquid formulation.

BACKGROUND OF THE INVENTION

Immune or gamma-interferon was originally classified on a physical basis as Type II Interferon due to its lability to acid treatment and/or heating to 56° C. This operational classification distinguished it from virus-induced or Type I Interferons (alpha and beta) which, in general, are not acid or heat labile. As a result of the widespread availability of specific antisera against each of the major interferon classes (alpha, beta, and gamma), classification and distinction of each type is now usually made by serological or immunological methods. Despite this, gamma-interferon preparations are still identified as such by their rapid inactivation upon acid treatment. See, *The Interferon System*, 2nd edition, W. E. Stewart II, Springer-Verlag, New York, 1981.

Gamma-interferon has been employed in clinical studies for many years. The methods currently available for preparing gamma-interferon dosage forms comprises lyophilizing the gamma-interferon in combination with other ingredients for reconstitution with an appropriate diluent at the time of use. Because gamma-interferon is known to be acid labile, it has traditionally been handled at neutral or slightly alkaline pH. See, for example, U.S. Pat. No. 4,499,014 which dicloses reactivation of a lyophilized acidic gamma-interferon solution to a pH of 6 to 9. U.K. Patent Application GB 2119313A discloses lyophilized formulations of gamma-interferon reconstituted at pH 7.5. Neutral or slightly alkaline solutions of higher concentrations of gamma-interferon are unusable as injectable formulations because of the immediate formation of a visible precipitate. Such precipitates may cause thrombosis on administration or decrease potency. European Patent Application Publication No. 0196203 discloses reconstitution of lyophilized gamma-interferon to a pH of 4 to 6.0.

An object of the present invention is to provide a biologically active, stable liquid formulation of gamma-interferon for use in injectable applications. Another object of this invention is to provide a formulation which does not require prior lyophilization of a gamma-interferon composition. It is another object of this invention to prevent dimer and oligomer formation consequent to lyophilization of gamma-interferon. Yet another object of this invention is to provide a liquid formulation containing biologically active gamma-interferon having improved stability. Still another object of this invention is to provide a liquid formulation permitting storage for a long period of time in a liquid state facilitating storage and shipping prior to administration. Still another object of this invention is to reduce aggregation of gamma-interferon, particularly that associated with heating. Another object of this invention is to provide a liquid formulation resistant to fluctuations in temperature. Yet another object of this invention is the elimination from the preparation of a bulking or stabilizing agent such as human serum albumin (HSA). Still another object of this invention is to reduce potential contamination by other proteins and other blood contaminants which may be associated with human serum albumin. Yet another object of this invention is to provide a liquid formulation which is easily made and administered having eliminated lyophilization and reconstitution steps. Yet another object of this invention is to provide a pharmaceutical composition containing non-lyophilized gamma interferon that can be produced less expensively.

SUMMARY OF THE INVENTION

The objects of this invention are accomplished by a liquid pharmaceutical composition comprising an effective amount of biologically active non-lyophilized gamma-interferon. The liquid pharmaceutical composition may additionally include a buffer capable of maintaining the pH of the liquid formulation within the range of 4.0 to 6.0, a stabilizing agent and a nonionic detergent. In a preferred embodiment of the liquid formulation of this invention the pH will be in the range of 4.5 to 5.5, preferably at pH 5.0. The gamma-interferon of this invention is not lyophilized but, rather, once prepared from sources using methods known to the ordinarily skilled artisan is included directly in the formulation of this invention. The stabilizing agent of this invention is typically a polyhydric sugar alcohol. It was not appreciated until this invention that a liquid formulation of gamma-interferon could be made which retains biological activity, has a long shelf-life and can be administered therapeutically without lyophilization and reconstitution. In addition, it was not appreciated until this invention that a liquid formulation of gamma-interferon at pH of from 4 to 6 would decrease aggregation, reduce thermal unfolding of the protein and maintain biological activity. It was also not appreciated until this invention that a non-lyophilized liquid formulation at pH 5.0 could have an extended shelf life. Accordingly, the invention is directed to a liquid pharmaceutical composition comprising an effective amount of non-lyophilized gamma interferon for therapeutic administration.

DETAILED DESCRIPTION

Gamma interferon and its methods of preparation, including synthesis in recombinant cell culture, are well known (EP 77, 670A and 146, 354A). Included within the scope of gamma-interferon are gamma interferon from recombinant or native sources as well as gamma-interferon variants, such as amino acid sequence variants, e.g., Cys-Tyr-Cys or desCys-Tyr-Cys amino terminal species. Also included are other insertions, substitutions or deletions of one or more amino acid residues, glycosylation variants, unglycosylated gamma-interferons, organic and inorganic salts and covalently modified derivatives of gamma-interferon. The effective amount of gamma-interferon to be formulated in the liquid composition is selected based on several variables, including the disease to be treated and therapeutic regimen. Generally the gamma-interferon has an activity in a standard bioassay in the range of $1 \times 10^6$ to $2 \times 10^7$ U/mg protein or more.

Examples of the polyhydric sugar alcohols to be used as the stabilizer in the present invention to insure isotonicity of the composition are those of trihydric or higher, such as glycerin, erythritol, arabitol, xylitol, sorbitol and mannitol. These polyhydric sugar alcohols can be used alone or in a combination thereof. In view of stabilization of interferon, the sugar alcohol is formulated in an amount of 1% to 25% by weight and preferably, 2% to 5% by weight taking into account the amounts of the other ingredients.

The organic acid buffers to be used in the present invention to maintain the pH in the range of about 4.0 to 6.0 and preferably from 4.5 to 5.5 can be conventional buffers of organic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium gluconate mixture, gluconic acid-sodium hydroxide mixture, gluconic acid-potassium gluconate mixture, etc.), oxalate buffers (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). It is noteworthy that inorganic acid buffers such as phosphate buffers which have been used traditionally do not maintain the pH of the liquid formulation at the desired pH.

Examples of the non-ionic detergents include such surfactants as pluronics, for example, polysorbate 80 and polysorbate 20. The non-ionic detergent is present in a range of 0.05 mg/mL with a preferred range of about 0.07 to 0.2 mg/mL and a most preferred amount of about 0.1 mg/mL.

The liquid formulation of this invention at a pH of 4 to 6, preferably 4.5 to 5.5 and most preferably at pH 5, demonstrates limited aggregation upon warming. Rather than being labile the liquid formulation of this invention is stable for prolonged periods. The formulation of this invention may be stored in a liquid state at various temperatures. A preferred storage temperature is in the range of $-20°$ C. to $30°$ C. with a most preferred temperature storage range of about between $2°$ and $8°$ C. All of the components are important for maintenance of biological activity and physical stability. Furthermore, the liquid formulation of this invention will retain biological activity and physical stability without freezing. This avoids potential aggregation upon thawing.

The following examples illustrate the present invention, but are not to be construed to limit the scope of the invention.

EXAMPLE 1

Liquid Formulation

Human recombinant gamma-interferon ($20 \times 10^6$ U/mg) was formulated by adding either 1.0 or 0.2 mg/mL to: succinic acid (0.27 mg/mL); disodium succinate (0.73 mg/mL); mannitol (40 mg/mL); polysorbate 20 (0.1 mg/mL); and a sufficient quantity of Water For Injection (USP). This liquid formulation was found to exhibit a long shelf life when maintained at a storage temperature of about between $2°$ and $8°$ C. in a liquid state. The succinate buffer maintained the liquid formulation at pH 5.0. The non-ionic detergent prevented aggregation during shipping and handling. The sugar rendered the formulation isotonic without the need for the addition of salts, which have been shown to cause aggregation of gamma-interferon. And further, the sugar appears to stabilize the pharmaceutical composition of this invention (compare the succinate/mannitol lyophilized formulation to the HSA/phosphate lyophilized formulation).

The liquid formulation of this invention using 0.2 mg/mL of non-lyophilized gamma-interferon was compared to two other lyophilized formulations of gamma-interferon. As seen in Table I below, the loss of bioactivity reflected in the rate constants was ten-fold greater for the succinate/mannitol lyophilized formulation and five-fold greater for HSA/phosphate lyophilized formulation than the liquid formulation of this invention. These changes in the bioactivity are reflected in the rate constant which is the slope of the line resulting from a plot of the natural logarithm of the loss of bioactivity of the gamma-interferon formulation versus time. Bioactivity was measured using a viral protection assay known to the ordinarily skilled artisan. The lyophilized compositions were stored in lyophilized form and were reconstituted at various times to determine the bioactivity remaining in the lyophilized preparation. The shelf life of the liquid formulation of this invention was considerably greater than that of the lyophilized formulations. The greater shelf life of the liquid formulation relative to the lyophilized formulation listed in Table 1 shows that the liquid formulation of this invention retains biological activity ten times longer than the lyophilized compositions.

TABLE 1

Comparative Stability of Gamma-Interferon Formulated at 0.2 mg/mL[1]

| Formulation | Study (months) | Rate Constant $\times 10^{-3}$ | Relative Shelf Life (days)[2] |
|---|---|---|---|
| Succinate/Mannitol Lyophilized | 6 | 2.854 | 1 |
| Succinate/Mannitol Liquid | 4 | 0.205 | 10 |
| HSA/Phosphate Lyophilized[3] | 3 | 1.038 | 5 |

[1] Based on real time $5°$ C. data.
[2] A comparison of the relative stability based on the bioactivity of the three formulations with the succinate/mannitol lyophilized composition being arbitrarily set at 1.
[3] This formulation was prepared by mixing 0.20 mg lyophilized gamma-interferon, 10 mg HSA, 5 mM sodium phosphate pH 7.0 and reconstituted with 0.9% saline.

A similar comparative study was carried out for the liquid formulation of this invention using 1.0 mg/mL of non-lyophilized human recombinant gamma-interferon. Once again, as shown in Table 2, the loss of bioactivity was greater for the lyophilized formulation than for the liquid formulation of this invention. Table 2 also shows that the shelf life of the liquid formulation of this invention was three times greater than that of the lyophilized formulation.

TABLE 2

Comparative Stability of Gamma-Interferon Formulated at 1.0 mg/mL[1]

| Formulation | Study Time (months) | Rate Constant $\times 10^{-3}$ | Relative Shelf Life (days)[2] |
|---|---|---|---|
| Succinate/Mannitol | 14 | 0.485 | 1 |

TABLE 2-continued

Comparative Stability of Gamma-Interferon Formulated at 1.0 mg/mL[1]

| Formulation | Study Time (months) | Rate Constant × 10−3 | Relative Shelf Life (days)[2] |
|---|---|---|---|
| Lyophilized Succinate/ Mannitol Liquid | 14 | 0.179 | 3 |

[1] Based on real time 5° C. data.
[2] A comparison of the relative stability based on the bioactivity of the two formulations with the succinate/mannitol lyophilized composition being arbitrarily set at 1.

We claim:

1. A stable liquid pharmaceutical composition consisting essentially of an effective amount of gamma-interferon not subjected to prior lyophilization, a buffer maintaining the pH within the range of 4.0 to 6.0, a stabilizing agent, a non-ionic detergent and water, in which said gamma-interferon essentially retains its physical stability and biological activity during storage at a temperature of between about 2° and about 8° C. for a period of at least 14 months.

2. The liquid pharmaceutical composition of claim 1 wherein the buffer is an organic acid buffer.

3. The liquid pharmaceutical composition of claim 2 wherein the organic acid buffer is selected from the group consisting of citrate, succinate, tartrate, fumarate, gluconate, oxalate, lactate and acetate.

4. The liquid pharmaceutical composition of claim 1 wherein the stabilizing agent is a polyhydric sugar alcohol.

5. The liquid pharmaceutical composition of claim 4 wherein the polyhydric sugar alcohol is selected from the group consisting of glycerin, erythritol, arabitol, xylitol, sorbitol and mannitol.

6. The liquid pharmaceutical composition of claim 5 wherein the sugar alcohol is added in an amount of about 1% to 25% by weight based on the composition.

7. The liquid pharmaceutical composition of claim 5 wherein the sugar alcohol is added in an amount of about 2% to 5% by weight based on the composition.

8. The liquid pharmaceutical composition of claim 1 wherein the non-ionic detergent is selected from the group consisting of polysorbate 20 and polysorbate 80.

9. The liquid pharmaceutical composition of claim 1 wherein the pH of the liquid composition is in the range of 4.5 to 5.5.

10. The liquid pharmaceutical composition of claim 1 wherein the pH of the liquid composition is at a pH of 5.0.

11. The liquid pharmaceutical composition of claim 1 which is sterile.

12. The liquid pharmaceutical composition of claim 1 which is isotonic to blood.

13. The liquid pharmaceutical composition of claim 1 wherein the gamma-interferon is human recombinant gamma-interferon.

14. The liquid pharmaceutical composition of claim 13 wherein the activity of the human recombinant gamma-interferon is in the range of $1 \times 10^6$ to $2 \times 10^7$ U/mg protein.

15. The liquid pharmaceutical composition of claim 14 wherein comprising a succinate buffer, and mannitol as a stabilizing agent.

16. The liquid pharmaceutical composition of claim 13 comprising 0.2 mg/ml human recombinant gamma-interferon.

17. A process for stabilizing gamma-interferon in liquid pharmaceutical compositions so that it essentially retains its physical stability and biological activity during storage at a temperature of between about 2° and about 8° C. for a period of at least 14 months, consisting essentially of admixing an effective amount of previously not lyophilized gamma-interferon with a buffer maintaining the pH within the range of 4.0 to 6.0, a stabilizing agent, a non-ionic detergent and water.

* * * * *